(12) United States Patent
Ichihashi (10) Patent No.: US 6,577,889 B2
(45) Date of Patent: Jun. 10, 2003

(54) RADIOGRAPHIC IMAGE DIAGNOSIS APPARATUS CAPABLE OF DISPLAYING A PROJECTION IMAGE IN A SIMILAR POSITION AND DIRECTION AS A FLUOROSCOPIC IMAGE (75) Inventor: Masahide Ichihashi, Otawara (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 09/977,504

(22) Filed: Oct. 16, 2001

(65) Prior Publication Data

US 2002/0045817 A1 Apr. 18, 2002

(30) Foreign Application Priority Data

Oct. 17, 2000 (JP) ....................................... 2000-316407

(51) Int. Cl.[7] ................................................ A61B 5/05
(52) U.S. Cl. .......................... 600/425; 600/427; 378/63
(58) Field of Search ................................. 600/425, 424, 600/407, 427; 378/205, 196, 42, 63

(56) References Cited

U.S. PATENT DOCUMENTS 6,149,592 A * 11/2000 Yanof et al. ................ 600/427
6,389,104 B1 * 5/2002 Bani-Hashemi et al. . 378/98.12
2001/0036245 A1 * 11/2001 Kienzle, III et al. ............. 378/4
2002/0041654 A1 * 4/2002 Hayashi ....................... 378/196

FOREIGN PATENT DOCUMENTS

JP 1-204650 8/1989
JP 8-332191 12/1996

* cited by examiner

Primary Examiner—Shawna J Shaw
(74) Attorney, Agent, or Firm—Oblon, Spivak, McClelland, Maier & Neustadt, P.C.

(57) ABSTRACT

A radiographic image diagnosis apparatus includes a photographing unit having a radiation source and a 2D radiation detector to generate data of a fluoroscopic image of an object to be examined. Volume data is generated on the basis of the data of plurality of fluoroscopic images of the object at different angles which are acquired by the photographing unit. A measuring mechanism measures the position and angle of the photographing unit with respect to the object. Projection image data is generated from the volume data on the basis of the position and angle of the photographing unit which are measured by the measuring mechanism. The volume data is then displayed. This makes it possible to display the projection image with substantially the same position and direction as those of a fluoroscopic image.

25 Claims, 5 Drawing Sheets

RADIOGRAPHIC IMAGE DIAGNOSIS APPARATUS CAPABLE OF DISPLAYING A PROJECTION IMAGE IN A SIMILAR POSITION AND DIRECTION AS A FLUOROSCOPIC IMAGE

CROSS-REFERENCE TO RELATED APPLICATIONS

This application is based upon and claims the benefit of priority from the prior Japanese Patent Application No. 2000-316407, filed Oct. 17, 2000, the entire contents of which are incorporated herein by reference.

BACKGROUND OF THE INVENTION

1. Field of the Invention

The present invention relates to a radiographic image diagnosis apparatus suitable for Interventional Radiology as a low invasive treatment.

2. Description of the Related Art

Recently, in the medical field, a great deal of attention has been paid to the idea of low invasive treatments or minimally invasive treatments intended to minimize the burden on patients in treatments.

Under the circumstances, Interventional Radiology (to be abbreviated as IVR) has become popular, in which an operator, for example, forms a blood vessel, injects an anticancer agent, or embolizes a blood vessel as a source of nourishment for a tumor cell while operating a treatment member such as a catheter inserted into the patient's body under X-ray fluoroscopy. X-ray diagnosis apparatuses, X-ray CT apparatuses, and the like dedicated to IVR have been developed.

Many IVR techniques are currently designed to insert catheters into blood vessels and perform various treatments. Examples of these techniques are: a technique of inserting a catheter having a balloon attached to its distal end into a blood vessel of a patient, guiding the distal end to an occluded blood vessel portion under X-ray fluoroscopy, and inflating the balloon, thereby expanding the occluded blood vessel; a technique of guiding a catheter to a bleeding region, and injecting a blood coagulant from the distal end of the catheter to occlude the bleeding blood vessel; a technique of guiding the distal end of a catheter to a region near a cancerous cell and occluding a blood vessel that feeds nourishment to the cancerous cell; and a technique of occluding a blood vessel after administering an anticancer agent from the distal end of a catheter. Recently, a technique of inserting a metal coil to an aneurysm through a catheter and occluding the aneurysm has recently been established.

Such an IVR technique allows a surgeon to perform an operation without trephination or celiotomy, and hence the burden on the patient is greatly reduced, and the patient can quickly recuperate from the operation.

An operator generally inserts a catheter from the femoral artery of a patient (object) and moves its distal end to a head portion, chest portion, abdominal portion, or the like as a treatment target region while observing an X-ray fluoroscopic image. In X-ray photographing, since the operator cannot observe a blood vessel without contrast medium administration, he/she grasps the blood vessel structure with an image photographed upon injection of a contrast medium into the blood vessel. More specifically, the operator injects the contrast medium from the distal end of the catheter into the blood vessel, and checks how the blood vessel runs while sequentially observing the contrasted blood vessel as an X-ray fluoroscopic image.

Since the injection of a contrast medium increases the physical burden on the patient (object), it is required to minimize the total amount of contrast medium. For this reason, the operator reuses a contrasted image of a blood vessel photographed upon injection of a contrast medium as a guide image, instead of sequentially injecting the contrast medium as the catheter moves, and displays this guide image and a real-time fluoroscopic image on a display unit, thereby assisting the movement of the catheter. This guide image is generally called a road map image.

In moving the catheter in practice, the operator inserts a guide wire opaque against X-rays into the catheter, and moves the guide wire first while monitoring the distal end of the guide wire with an X-ray fluoroscopic image. The operator then moves the catheter to the distal end position of the guide wire. The operator repeats this operation to move the catheter to a desired region.

As the second method, the method disclosed in Jpn. Pat. Appln. KOKAI Publication No. 1-204650 is known, in which a 2D contrasted image of a blood vessel is generated before the movement of a catheter, and the contrasted blood vessel image is used as a road map image. This road map image and a real-time image during X-ray fluoroscopy are superimposed on each other and displayed, thereby moving the catheter to a target region.

As the third method, the method disclosed in Jpn. Pat. Appln. KOKAI Publication No. 8-332191 is known, in which a target route marker is set in 3D image data of an object which includes the insertion position of a catheter and a target region to which the distal end of the catheter must traverse, and the catheter is guided to the target region along this target route maker.

In the first method, however, the 2D contrasted blood vessel image as a road map image does not always coincide in photographing direction with a fluoroscopic image during actual movement of the catheter. For this reason, it takes much time to execute this method, resulting in an increase in burden on the operator as well as the patient.

In the second method, when a blood vessel route changes relatively smoothly, the catheter can be moved very accurately along the blood vessel route. If, however, the blood vessel route changes in a complicated manner or branches off, it is not easy to move the catheter. In this case, the operator must handle the catheter with great care. Furthermore, in the third method, it is difficult to associate a blood vessel with the distal end of the catheter on a display screen, and hence the operator who operates the catheter is still required to have great knowledge and experience.

BRIEF SUMMARY OF THE INVENTION

It is an object of the present invention to provide information that effectively assists moving operation of a catheter in a radiographic image diagnosis apparatus.

A radiographic image diagnosis apparatus according to the present invention includes a photographing unit having a radiation source and a 2D radiation detector to generate data of a fluoroscopic image of an object to be examined. Volume data is generated on the basis of the data of a plurality of fluoroscopic images of the object at different angles which are acquired by the photographing unit. A measuring mechanism measures the position and angle of the photographing unit with respect to the object. Projection image data is generated from the volume data on the basis of the position and angle of the photographing unit which are measured by the measuring mechanism. The volume data is then displayed. This makes it possible to display the projection image with substantially the same position and direction as those of a fluoroscopic image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given below and the detailed description of the embodiments given below, serve to explain the principles of the invention.

DETAILED DESCRIPTION OF THE INVENTION

A radiographic image diagnosis apparatus according to an embodiment of the present invention will be described in detail below with reference to FIGS. 1 to 7.

Figure 1:
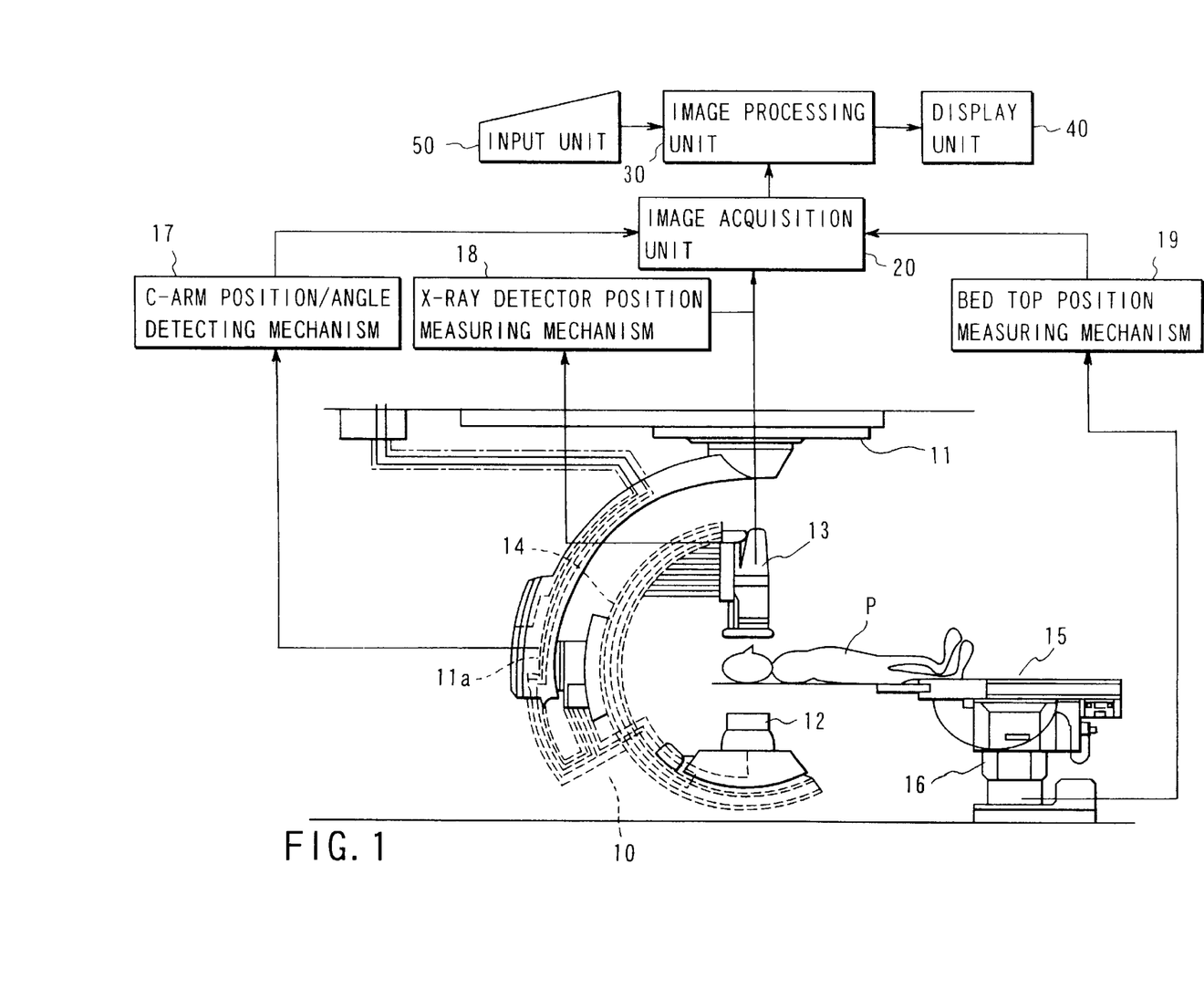
FIG. 1 is a view showing the arrangement of a radiographic image diagnosis apparatus according to an embodiment.

FIG. 1 shows the arrangement of the radiographic image diagnosis apparatus according to this embodiment. The radiographic image diagnosis apparatus of this embodiment includes, as main components, an X-ray image photographing unit 10 for photographing a 2D fluoroscopic image of an object P, an image acquisition unit 20 for acquiring the image data photographed by the X-ray image photographing unit 10 and temporarily recording the data, an image processing unit 30 for processing the image data acquired by the image acquisition unit 20, and a display unit 40 for displaying the image processed by the image processing unit 30. Note that as the image acquisition unit 20 and image processing unit 30, for example, general personal computers or workstations can be used.

The X-ray image photographing unit 10 has a photographing unit made up of an X-ray tube 12 and 2D X-ray detector 13. The photographing unit is supported by a support mechanism. The support mechanism is comprised of, for example, a support portion 11 movably mounted on a ceiling portion, a support arm 11a extending from the support portion 11, and a C-arm 14 supported by the support arm 11a and bent in the shape of "C". The photographing unit is mounted on the C-arm 14. The object P placed on a top 15 of a bed 16 is interposed between the X-ray tube 12 and the 2D X-ray detector 13. A C-arm position/angle detecting mechanism 17 is configured to measure the positions and angles of the X-ray tube 12 and 2D X-ray detector 13 in photographing the object P, i.e., the position and rotational angle of the C-arm 14 serving as a photographing unit. An X-ray detector position measuring mechanism 18 is configured to measure the distance between the 2D X-ray detector 13 and the object P or X-ray tube 12. A bed top position measuring mechanism 19 is configured to measure the position of the top 15.

The X-ray tube 12 and 2D X-ray detector 13 attached to the C-arm 14 are arranged to oppose each other through the object P. The 2D X-ray detector 13 is retractably mounted to adjust the distance to the X-ray tube 12. The C-arm 14 is supported by the support arm 11a such that it can rotate around the body axis of the object P and move in an arc along the longitudinal direction of the C-arm 14. Note that an Ω arm bent in the shape of "Ω" may be used in placed of the C-arm 14.

Referring to FIG. 1, the 2D X-ray detector 13 is comprised of an X-ray image intensifier for outputting a fluoroscopic image of the object P or the like, which is obtained by weak X-ray irradiation, as a bright optical image, and a TV camera for sensing an image on the output phosphor surface of the X-ray image intensifier. However, the present invention is not limited to this arrangement. For example, the 2D X-ray detector 13 may be formed by a plurality of X-ray image detectors in a matrix, each of which is made of a multilayer member formed by optically coupling a phosphor screen and a semiconductor optical sensor.

The X-rays emitted from the X-ray tube 12 and transmitted through the object P are detected by the 2D X-ray detector 13 and subjected to proper pre-processing. The resultant data is output as fluoroscopic image data. The fluoroscopic image data obtained by the 2D X-ray detector 13 is loaded and recorded by the image acquisition unit 20, together with the information of the position and rotational angle of the C-arm 14 which is detected by the C-arm position/angle detecting mechanism 17, i.e., the information of the positions and angles of the X-ray tube 12 and 2D X-ray detector 13 with respect to the object P. Likewise, the data of the distance between the 2D X-ray detector 13 and the object P or X-ray tube 12, obtained from the X-ray detector position measuring mechanism 18, and the position data of the top 15, obtained from the bed top position measuring mechanism 19, are also loaded and recorded by the image acquisition unit 20, together with the image data. The image data loaded in the image acquisition unit 20 is supplied to the image processing unit 30, together with the information of the positions and angles of the X-ray tube 12 and 2D X-ray detector 13, the position information of the 2D X-ray detector 13, and the position information of the top 15.

The image processing unit 30 includes a section for reconstructing the fluoroscopic data of the object P obtained by the 2D X-ray detector 13 into volume data on the basis of the angle/position information in photographing operation, a section for generating clinical/analytical information about the object P from the reconstructed volume data, a section for executing subtraction processing for a fluoroscopic image, a section for performing image superimposition and rotation processing, and a section for computing the position or direction of a member imprinted on a fluoroscopic image. The image processing unit 30 therefore incorporates a processor having a CPU as a main component, a memory required for processing, and the like.

The image information, clinical/analytical information, and the like generated by the image processing unit 30 are displayed on the display unit 40. Note that position information, numerical information, and the like displayed on the display unit 40 are input through the image processing unit 30 by using an input unit 50 such as a mouse, track ball, or keyboard. In addition, the input unit 50 is used to input various instructions to the image processing unit 30.

Image processing and image display to be performed when a treatment member such as a catheter is inserted into a patient (object P) and a check and treatment are performed by using the radiographic image diagnosis apparatus having the above arrangement will be described next with reference to the flow chart of FIG. 2.

A treatment member such as a catheter is generally inserted into the object P from the femoral artery located apart from a head portion or chest as a target region to be checked or treated. The catheter is an elongated hollow tube made of rubber or a synthetic resin, and its distal end has a hole for injecting a contrast medium. When this distal end is to be guided to a target region of the object P, the catheter is used together with a guide wire extending through the hollow portion of the catheter. This guide wire is made of a material having a relatively low X-ray transmittance, and hence can be clearly identified under X-ray fluoroscopy.

Figure 2:
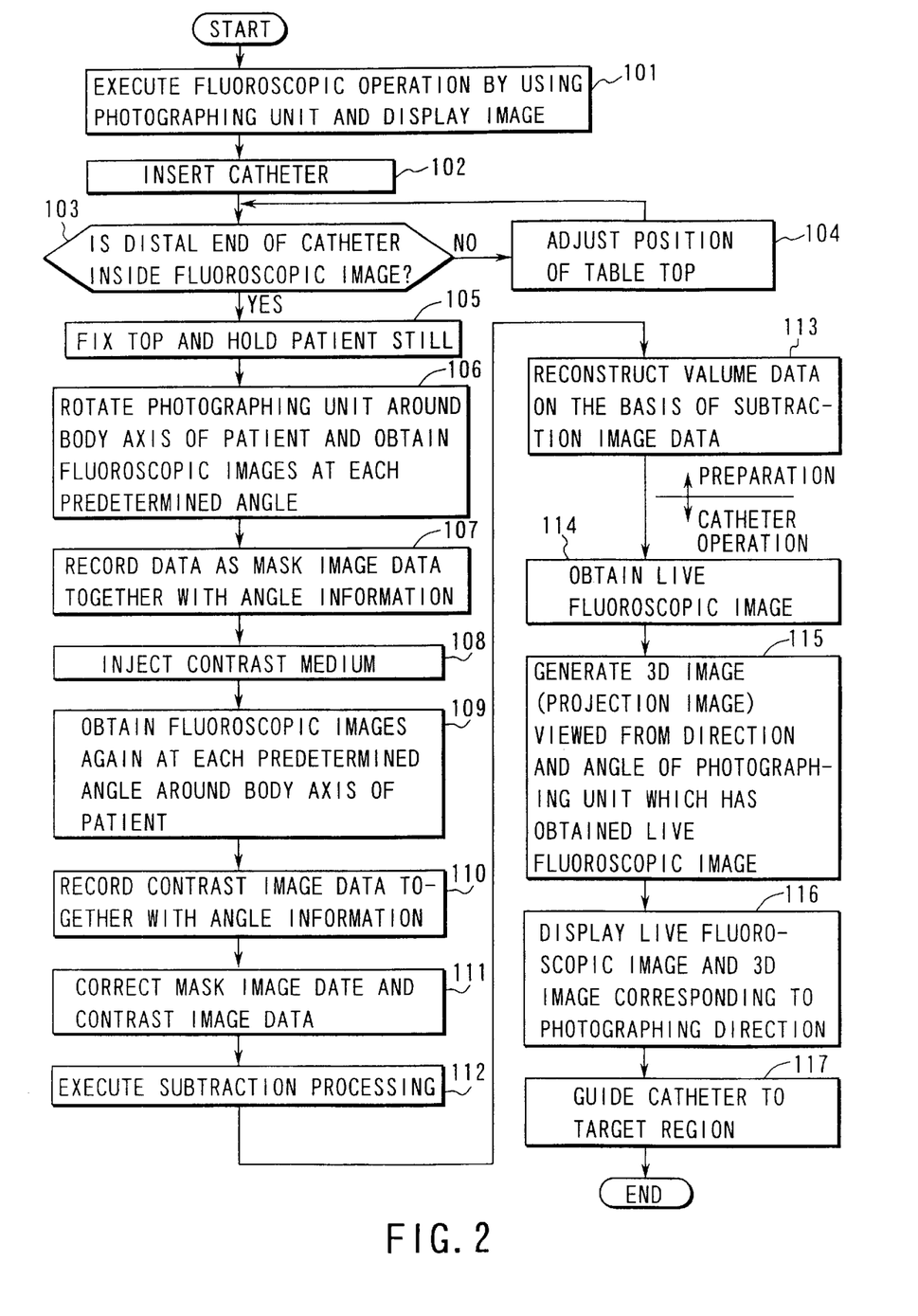
FIG. 2 is a flow chart for explaining a procedure for performing a check or treatment by using the radiographic image diagnosis apparatus according to this embodiment.

Referring to the flow chart of FIG. 2, in step 101, for example, the X-ray tube 12 attached to the C-arm 14 is placed in front of the object P to set the X-ray tube 12 and 2D X-ray detector 13 parallel to each other on the two sides of the object P lying on his/her back on the top, thereby preliminarily performing fluoroscopic operation. The resultant fluoroscopic image is then displayed on the display unit 40.

In step 102, the operator inserts a catheter with a guide wire from a predetermined position while observing the fluoroscopic image of the object P displayed on the display unit 40. The operator then repeatedly moves the top 15 of the bed 16 in the body axis direction of the object P and a direction perpendicular to the body axis, as needed, (step 104) to obtain a fluoroscopic image including a target region while checking whether the distal end of the catheter is located in the fluoroscopic image (step 103).

In operating the catheter, the operator gradually moves the distal end of the guide wire first toward the target region (e.g., the carotid artery) in a blood vessel under X-ray fluoroscopy, and then gradually moves the catheter along the guide wire in the blood vessel with the distal end of the guide wire as a guide, thereby guiding it to tit the carotid artery.

When the distal end of a catheter 21 reaches a portion near the target region, the operator acquires data of a plurality of 2D fluoroscopic images at different angles, which are required to construct a 3D image of the object P including the target region, in the following manner.

In step 105, the top 15 is fixed and the object P placed on the top 15 is held still. In step 106, the operator makes the X-ray tube 12 emit X-rays at each predetermined angle while rotating the C-arm 14 around the body axis of the object P with the X-ray tube 12 and 2D X-ray detector 13 opposing each other in a direction perpendicular to the body axis of the object P. In general, this rotation range is about 180° to 200° owing to the performance of the X-ray image photographing unit 10, and fluoroscopic images are photographed at a frame rate of 8 to 30 frames per second at each predetermined angle in this range. In step S107, the data of the fluoroscopic images photographed at each predetermined angle are loaded and recorded by the image acquisition unit 20, together with the angle information detected by the C-arm position/angle detecting mechanism 17. The fluoroscopic images photographed in this manner are so-called mask images before the injection of a contrast medium which are required to form subtraction images, and include a target region, in the absence of a contrast medium, to which a treatment member such as a catheter must traverse.

In step 108, the operator injects a contrast medium into a blood vessel of the object P through the catheter from its distal end. Under the same photographing conditions as those for the mask images, the operator acquires the data of fluoroscopic images photographed at each predetermined angle by making the X-ray tube emit X-rays at each predetermined angle while rotating the C-arm 14 around the body axis of the object P with the top 15 being fixed and the object P being held still (step 109). The fluoroscopic images photographed in this manner are required to form subtraction images. The data of the fluoroscopic images after the injection of the contrast medium are also loaded and recorded by the image acquisition unit 20, together with the angle information detected by the C-arm position/angle detecting mechanism 17 (step 110).

In step 111, the data of the obtained mask images (the fluoroscopic images before the injection of the contrast medium) and the data of the fluoroscopic images after the injection of the contrast medium are subjected to correction processing to obtain clear display images by, for example, removing sensitivity irregularity, background noise, geometrical distortion, and the like. These fluoroscopic images before and after the injection of the contrast medium, which have undergone this correction processing, are subjected to logarithmic difference (subtraction) processing for each angle information in step 112, thereby generating subtraction image data with emphasized images of the blood vessel into which the contrast medium is injected. The subtraction image data include 3D information generated at each predetermined angle. These data are used to reconstruct volume data as a source of a road map image required for catheter operation.

In step 113, the image processing unit 30 reconstructs volume data representing a blood vessel structure on the basis of each subtraction image data corresponding to each predetermined angle of the C-arm 14 that has been rotated around the object P. In step 114, a fluoroscopic image is obtained while the object P placed on the top 15 is held still. In step 115, volume data is projected with the same viewpoint and the same direction as those when the operator saw the detector center from the X-ray focal point in obtaining this fluoroscopic image, thereby generating 3D image data (projection image data). In step 116, the fluoroscopic image and 3D image data at this point of time are displayed on the display unit 40. This fluoroscopic image is a real-time live image. In step 117, the operator guides the catheter to the target region while seeing the fluoroscopic image and 3D image.

Figure 3:
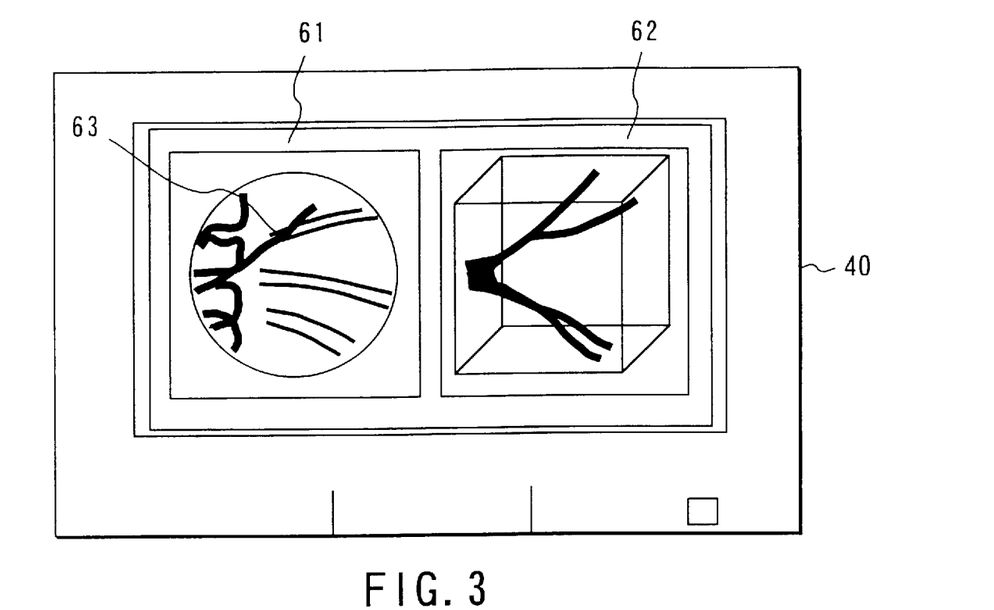
FIG. 3 is a view showing an example of how a fluoroscopic image and a reconstructed 3D image are displayed in this embodiment.

FIG. 3 shows an example of display operation in step 116. A fluoroscopic image 61 and 3D image 62 are placed side by side on the same screen. The 3D image 62 displayed on the display unit 40 is a 2D projection image which can observed from a desired direction. This 2D projection image is, for example, a volume rendering image. However, the present invention is not limited to this. For example, this image may be displayed as a surface display image projected by a maximum intensity projection (MIP) technique, minimum intensity projection (MinIP) technique, sum-total intensity projection (integral projection) technique, or the like, or a virtual endoscope (fly-through) image.

As a projection technique, a so-called diffusion projection method is used in a limited manner, in which a plurality of rays are radially sent onto a projection surface with a viewpoint being set as a center, and voxel values on the respective rays are tracked. This operation is performed to re-create the photographing mechanism of the photographing unit in which a plurality of X-ray beams radially propagate from the X-ray focal point of the X-ray tube to the detectors. A projection viewpoint is set at a position on a volume data coordinate system which corresponds to the position of the X-ray focal point, and a projection surface is set at a position on the volume data coordinate system which corresponds to the positions of the detectors.

FIG. 3 shows the state where the fluoroscopic image 61 and 3D image (2D projection image) 62 are displayed side by side. However, the present invention is not limited to this. For example, the 3D image (2D projection image) 62 may be overlapped on the fluoroscopic image 61 at a predetermined ratio, or the fluoroscopic image 61 and the 3D image (2D projection image) 62 overlapping the fluoroscopic image 61 at a predetermined ratio may be displayed. The display unit 40 may be designed to display two images side by side on one display (e.g., a CRT monitor), or may have a plurality of displays on which the fluoroscopic image 61 and 3D image (2D projection image) 62 are separately displayed. Alternatively, a plurality of display units 40 each having one display may be prepared to separately display the fluoroscopic image 61 and 3D image (2D projection image) 62 on the respectively display units 40.

The display direction and position of the 3D image (2D projection image) 62 displayed on the display unit 40, i.e., the projection direction and viewpoint position with respect to the volume data, are set in accordance with the angle (RAO/LAO and CRA/CAU) of the C-arm 14 with respect to the object P upon photographing the fluoroscopic image 61, the position of the cylinder focal point or top 15, and the enlargement ratio/reduction ratio based on the distance between the object P and the X-ray tube 12 or between the object P and the 2D X-ray detector 13. Note that RAO (Right Anterior Oblique)/LAO (Left Anterior Oblique) represents an observation direction parallel to the object P. RAO indicates a case where the operator observes from the right side of the object P. LAO indicates a case where the operator observes from the left side of the object P.

When, for example, the operator observes the object P lying on his/her back on the top from the front side, RAO0. When the operator observes the object P from a 40° right direction, RAO40. CRA (Cranial)/CAU (Caudal) represents an observation direction in the body axis direction of the object P. CRA represents a case where the operator observes the object P from the upper side of the body axis. CAU represents a case where the operator observes the object P from the lower side of the body axis. When, for example, the operator observes the object P from the front side, CRA0, which is generally combined with an RAO/LAO notation to be expressed as RAO0CRA0.

Since these angle/position information and distance information are supplied from the C-arm position/angle detecting mechanism 17, X-ray detector position measuring mechanism 18, and bed top position measuring mechanism 19 to the image acquisition unit 20 every time photographing is performed by the X-ray tube 12 and 2D X-ray detector 13, the display direction and position of the 3D image (2D projection image) 62 displayed on the display unit 40 are updated on the basis of these pieces of information. That is, the position of the 3D image (2D projection image) 62 displayed on the display unit 40 relatively coincides with that of the photographed real-time fluoroscopic image 61. Assume that the positional relationship between a blood vessel and a catheter is not clear from the fluoroscopic image 61. In this case, if the operator photographs a fluoroscopic image while moving and rotating the C-arm 14 or moving the top 15 so as to grasp the positional relationship in more detail, the 3D image (2D projection image) 62 in a direction corresponding to the resultant angle and position is displayed.

By repeatedly executing such operation, the operator obtains road map information while referring to the 3D image (2D projection image) 62, and is assisted in finally guiding the catheter to a target region (e.g., the position of an aneurysm). Even if, therefore, the photographing angle or position of the X-ray image photographing unit 10 changes, the 3D image (2D projection image) 62 coinciding in line of sight with a fluoroscopic image is provided as a road map image almost in real time. The operator can easily operate the catheter by seeing the road map image. This reduces the burden on the object and operator.

Note that the photographing angle or position need not always be linked with the 3D image 62. For example, setting can be made to inhibit them from being linked with each other with initial settings of software. In this case, rotation, movement, enlargement/reduction, and the like of the 3D image 62 may be arbitrarily executed in accordance with an instruction from the input unit 50 regardless of the operation of the X-ray image photographing unit 10. The above subtraction processing is performed to facilitate boundary extraction, and mainly performed when a blood vessel or gullet is a target region. Depending on a target region, a 3D image may be reconstructed by using live image data instead of subtraction images. Note that an image of a catheter (guide wire) 63 is imprinted in the fluoroscopic image 61.

The technique of guiding the catheter to the target region by using the 3D image 62 in FIG. 3 as a road map image has been described with reference to the flow chart of FIG. 2. To set the 3D image (2D projection image) 62 formed on the basis of the real-time fluoroscopic image 61 in an optimal direction and position or in a direction suited to a check and treatment as a road map image, the operator must repeatedly photograph a fluoroscopic image while changing the angle or position of the C-arm 14 and enlargement/reduction ratio. In treating, for example, an aneurysm, in particular, the operator is required to quickly obtain an optimal photographing angle, position, enlargement/reduction ratio, and the like of the fluoroscopic image 61 for the treatment.

For this purpose, the 3D image 62 is generated in the above manner or a 3D image is generated on the basis of 3D image data about the same object P which have been acquired in advance, and the operator finds an optimal direction and angle for the movement of the catheter or a check or treatment by rotating and moving such a 3D image. Thereafter, the operator can set, for example, the position and angle of the C-arm and the distance to the 2D X-ray detector 13, which serve as components of the photograph unit, so as to obtain the fluoroscopic image 61 at the above position and angle.

That is, the viewpoint and line-of-sight direction of volume data can be arbitrarily set independently of the position and angle of the photograph unit by disconnecting the link between the fluoroscopic image and the 3D image 62.

With this operation, the operator moves the C-arm by moving the viewpoint and line-of-sight direction of the volume data so as to search for optimal values of the position and angle of the photograph unit. That is, a simulation can be done.

As described in steps 101 to 113 in FIG. 2, a 3D image of the object P is reconstructed by using the data obtained by photographing by the X-ray image photographing unit 10. However, the present invention is not limited to this. For example, such an image may be reconstructed on the basis of the data acquired by using various types of medical diagnosis apparatuses such as an X-ray CT apparatus, MRI apparatus, and ultrasonic diagnosis apparatus, which allow observation of the inside of a living body. The 3D image data in this case is also stored in the memory in the image processing unit 30.

Figure 5:
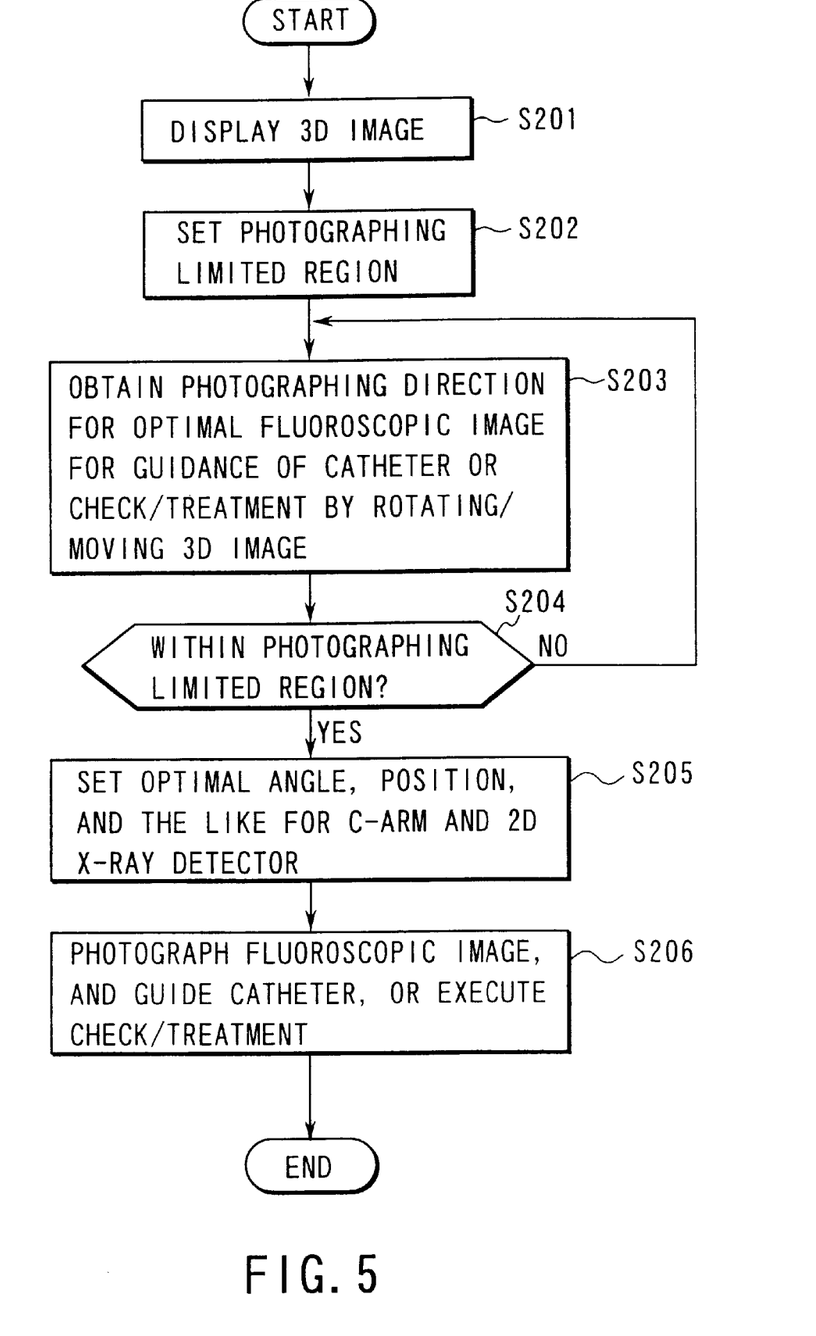
FIG. 5 is a flow chart showing a procedure for a fluoroscopic simulation according to this embodiment.

FIG. 5 is a flow chart showing a procedure for a simulation by the image processing unit 30. In step 201, a 3D image is displayed on the display unit 40. Note that the 3D image (2D projection image) 62 generated in step 113 in FIG. 2 is used for the sake of convenience. In this case, the 3D image 62 need not coincide with the fluoroscopic image 61 in relative position, angle, enlargement/reduction ratio, and the like from the beginning, and may be arbitrarily set by the input unit 50.

Note that a predetermined limitation is imposed on the degree of freedom of the movement of the photographing unit due to the structural limitation of the support mechanism of the C-arm 14 of the X-ray image photographing unit 10. A region which cannot be photographed by the photographing unit due to this structural limitation is called a photographing limited region (65 in FIG. 4) based on the structure of the photographing unit. In addition, the movement of the photographing unit is limited to prevent the X-ray tube 12 and 2D X-ray detector 13 from colliding with the object P. The region that cannot be photographed by the photographing unit based on the physique of the object will be referred to as a photographing limited region (64 in FIG. 4) based on the physique of the object. The data of the photographing limited regions 64 and 65 must be set in advance and stored in the image processing unit 30 or the like. In step 202, therefore, the photographing limited regions 64 and 65 are set and stored.

Figure 4:
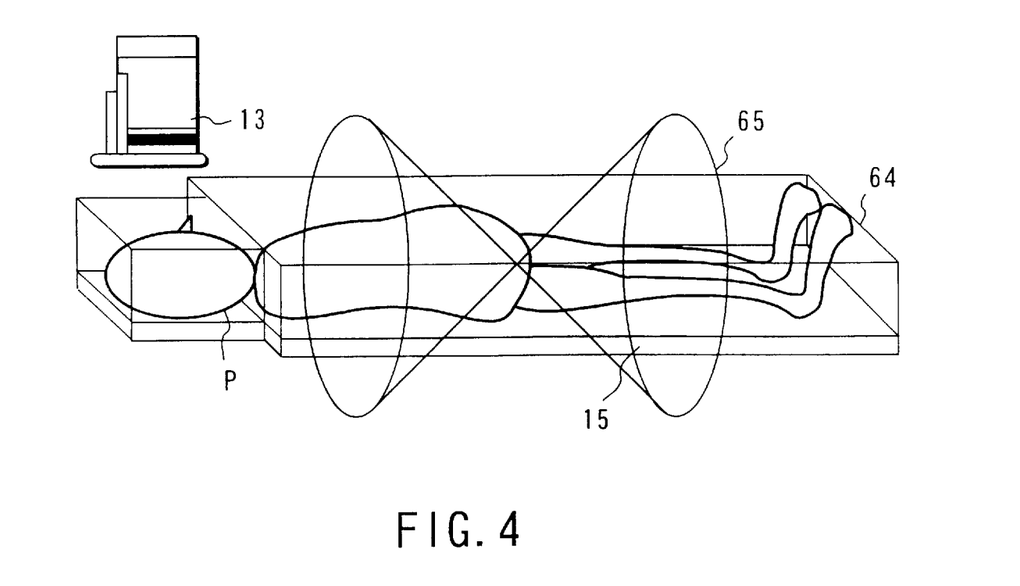
FIG. 4 is a view showing photographing limited regions in this embodiment.

The X-ray image photographing unit 10 is limited in terms of the specifications and performance such that the maximum rotational angle range of the C-arm 14 around the body axis of the object P is defined as 50° in the CRA direction, 45° in the CAU direction, 120° in the RAO direction, and 120° in the LAO direction, and the distance range in which the C-arm 14 can move with respect to the X-ray tube 12 of the 2D X-ray detector 13 is defined as 500 mm to 800 mm. Photographing cannot be done at any positions and angles outside this limitations. These conditions are based on the structure of the arm support mechanism of the X-ray image photographing unit 10. The photographing limited region 65 based on the structure is defined as an eigenvalue due to this condition.

This photographing limited region 65 based on the structure is defined in the absence of an object on the top 15. When the object P lies on the top 15, the photographing limited region 64 based on the physique of the object P appears. Since the photographing limited region 64 based on the physique of the object P is not fixed, such a region must be measured for each object or several standard patterns must be set for children, adults, fat persons, and the like.

For example, the photographing limited region 64 based on the physique of the object P is measured as follows. A patient (P) is asked to lie down on the top 15 in a state where IVR is executed, and the 2D X-ray detector 13 is brought to a position nearest to the surface of the object P. At this time, the distance between the 2D X-ray detector 13 and the top 15 is measured. For example, as shown in FIG. 4, the rectangular parallelepiped region defined by the area of the top 15 as a base and the obtained distance between the 2D X-ray detector 13 and the top 15 as a height is a region which the X-ray tube 12 cannot enter. As a result, this region becomes the photographing limited region 64 based on the physique of the object P.

With regard to the photographing limited region 64 based on the physique of the object P, the area of the top 15 is set as a base. If, however, the object P is wider than the top 15, the region must be corrected such that the base is defined by the maximum width of the object P and the length of the top 15. The photographing limited region 64 need not always be measured with the object P placed on the top 15 of the X-ray image photographing unit 10. The photographing limited region 64 may be constructed on the basis of the physique information of the object P which is input to the image processing unit 30 through the input unit 50. This photographing limited region 64 functions when the fluoroscopic image 61 at an optimal angle and position for a treatment is to be set by using the 3D image 62.

In step 203, the operator searches for an optimal angle and position for the guidance of the catheter or a check/treatment by rotating and moving the position and direction of the 3D image 62 displayed in step 201 with the mouse or trackball of the input unit 50. At this time, rotation and movement of the 3D image 62 are monitored in step 204. That is, as described above, the maximum rotational angle of the C-arm 14 and the movable range of the 2D X-ray detector 13 are limited by the specification and performance of the X-ray image photographing unit 10. For this reason, even if an optimal angle is found from the 3D image 62, no fluoroscopic image can be photographed when the C-arm 14 is located inside at least one of the photographing limited regions 64 and 65.

When, therefore, the rotational angle of the 3D image 62 falls within the photographing limited regions 64 and 65 (the rotation range of the C-arm 14 exceeds an allowable range), or the movable range of the 3D image 62 falls within the photographing limited regions 64 and 65 (the movable ranges of the C-arm 14 and top 15 exceed allowable ranges), rotation and movement beyond these ranges must be restricted. In addition, when an attempt is made to perform enlargement/reduction beyond the distance range between the X-ray tube 12 and the 2D X-ray detector 13, such enlarging/reducing operation beyond the range must be restricted.

Figure 6:
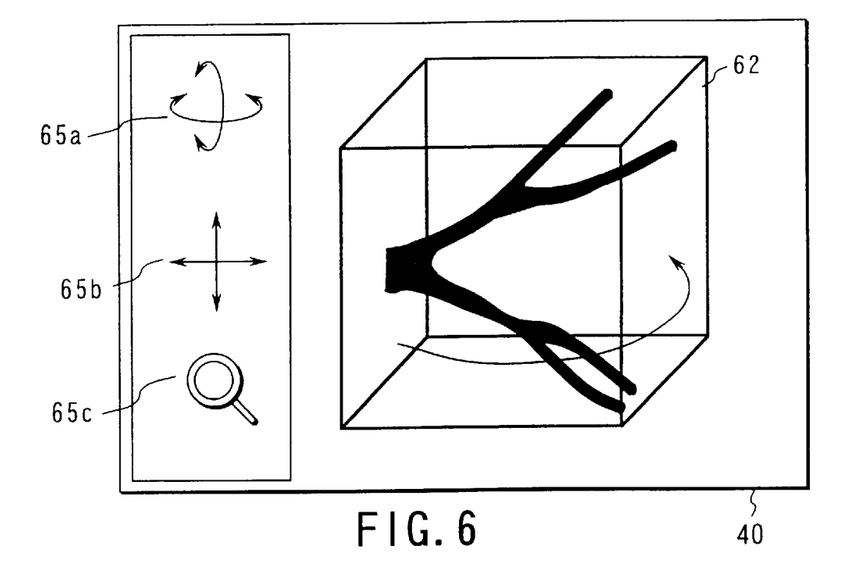
FIG. 6 is a view showing an operating section for rotation, movement, enlargement/reduction, and the like of a 3D image in this embodiment.

FIG. 6 shows an example of a window on the display unit 40 displaying operation buttons for the rotation, movement, enlargement/reduction, and the like of the 3D image 62. More specifically, three types of icons 65a, 65b, and 65c are displayed, together with the 3D image 62. When the operator selects a desired icon with the input unit 50, desired operation is executed. In this case, the icon 65a is used for rotation; the icon 65b, for movement; and the icon 65c, for enlargement/reduction. If the rotation, movement, and or like of the 3D image 62 exceeds the photographing limited region 64 by operating the icon 65a, 65b, or 65c, any further operation in the corresponding direction is restricted.

Figure 7:
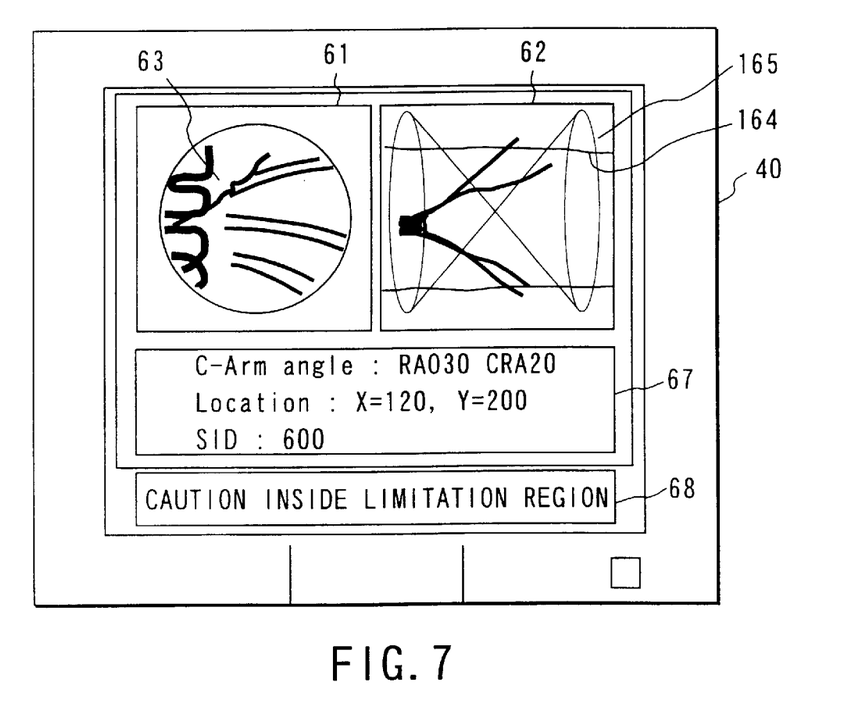
FIG. 7 is a view showing a display window in this embodiment.

Instead of restricting the operation of the 3D image 62, wire frame models 164 and 165 indicating the photographing limited regions 64 and 65 may be overlapped on the 3D image 62, as shown in FIG. 7. In this case, the wire frame models 164 and 165 indicate the inner and outer boundaries. If the inner parts of the wire frame models 164 and 165 are displayed in colors different from those of outer parts of the models, the operator can recognize the photographing limited region more clearly.

In addition, numerical values representing the observation direction of the 3D image 62, the position of the X-ray image photographing unit 10, the distance from the object P to the X-ray tube 12, and the like may be displayed on another display area 67 of the display unit 40. In operating the 3D image 62, the display colors of these numerical values may be changed depending on whether the image enters the photographing limited regions or not. Alternatively, various means may be provided to inform that the image has entered the photographing limited regions. For example, a message 68 informing that the image has entered the photographing limited regions or an alarm may be generated.

In step 204, it is checked whether the position and angle of the photographing unit which correspond to the viewpoint and projection direction have entered the photographing limited regions 64 and 65 upon rotation and movement of the 3D image 62. If they have entered the photographing limited regions 64 to 65, the flow returns to step 203 to repeat the above operation. If they are located outside the photographing limited regions 64 and 65, the flow advances to step 205 to control the position and angle of the photographing unit in accordance with the viewpoint and projection direction. The flow then advances to step 206 to guide the catheter or execute a check/treatment while obtaining the fluoroscopic image 61 at an optimal angle and position.

As described above, according to this embodiment, since the operator can know a region in which fluoroscopic images can be photographed in advance, he/she can perform fluoroscopic photographing operation upon setting, for example, an optimal projection angle for a check or treatment. This can therefore prevent photographing conditions such as a projection angle, position, and enlargement ratio from falling outside the photographing limited region 64, and hence can prevent determination of a projection angle from being redone. This makes it possible to shorten the time required for a check and treatment, thus reducing the burden on an object and operator.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A radiographic image diagnosis apparatus comprising:
   a photographing unit having a radiation source and a 2D radiation detector to generate data of a fluoroscopic image of an object to be examined;
   a volume data generating section configured to generate volume data on the basis of data of a plurality of fluoroscopic images of the object at different angles;
   a measuring mechanism configured to measure a position and angle of said photographing unit with respect to the object;
   a projection image data generating section configured to generate projection image data from the volume data on the basis of the position and angle of said photographing unit which are measured by said measuring mechanism, and
   a displaying unit configured to display the projection image data;
   wherein said projection image data generating section sets a viewpoint at a position on a volume data coordinate system which corresponds to a radiation focal point of said radiation detector which is determined by the position of said photographing unit, sets a projection direction corresponding to the angle of said photographing unit, radially sets a plurality of rays from the projection viewpoint with respect to the projections surface, and integrates values of the volume data along the plurality of rays, thereby generating the projection image data.

2. An apparatus according to claim 1, wherein the volume data represents a blood vessel structure.

3. An apparatus according to claim 1, wherein said volume data generating section comprises a section configured to subtract data of a fluoroscopic image before contrast radiography of a blood vessel and data of a fluoroscopic image after the contrast radiography of the blood vessel from each other.

4. An apparatus according to claim 1, wherein said displaying unit displays fluoroscopic image data photographed live by said photographing unit, together with the projection image data.

5. An apparatus according to claim 1, wherein said projection image data generating section projects the volume data with a viewpoint and a projection direction which correspond to the position and angle of said photographing unit which are measured by said measuring mechanism.

6. An apparatus according to claim 5, wherein said projection image data generating section radially sets a plurality of projecting rays with the viewpoint as a center and projects the volume data along the respective projecting rays.

7. An apparatus according to claim 1, wherein said displaying unit displays the fluoroscopic image data and the projection image data side by side.

8. An apparatus according to claim 1, wherein said display unit displays the fluoroscopic image data and the projection image data upon superposing the data.

9. An apparatus according to claim 1, wherein when the position and angle of said photographing unit which are measured by said measuring mechanism change, said projection image data generating section projects the volume data again to generate the projection image data corresponding to the changed position and angle of said photographing unit.

10. An apparatus according to claim 9, wherein said projection image data generating section projects the volume data with a viewpoint and a projection direction which correspond to the position and angle of said photographing unit which are measured by said measuring mechanism.

11. An apparatus according to claim 1, further comprising an input unit for inputting a user instruction to arbitrarily rotate the projection image data.

12. An apparatus according to claim 11, further comprising means for generating a control signal for changing the angle of said photographing unit with respect to the object in accordance with a direction of projection image data rotated by the user instruction.

13. An apparatus according to claim 1, wherein said measuring mechanism measures a distance between the object and said radiation source or between the object and said 2D radiation detector as well as the position and angle of said photographing unit.

14. An apparatus according to claim 13, wherein said projection image data generating section enlarges the projection image data at an enlargement ratio corresponding to the measured distance between the object and said radiation source or between the object and said 2D radiation detector.

15. An apparatus according to claim 13, wherein said display unit displays the projection image data at an enlargement ratio corresponding to the measured distance between the object and said radiation source or between the object and said 2D radiation detector.

16. A radiographic image diagnosis apparatus comprising:
- a photographing unit having a radiation source and a 2D radiation detector to generate data of a fluoroscopic image of an object to be examined;
- a support mechanism configured to movably support said photographing unit;
- a 3D image data generating section configured to generate 3D image data corresponding to a position and angle of said photographing unit with respect to the object;
- a photographing limited region data generating section configured to generate data of a first photographing limited region of said photographing unit which is limited by a structural limitation of said support mechanism, and data of a second photographing limited region of said photographing unit which is limited by a physique of the object; and
- a displaying unit configured to display the data of the first and second photographing limited regions, together with the 3D image data.

17. An apparatus according to claim 16, wherein said photographing limited region data generating section comprises a storage unit for storing the data of the first and second photographing limited regions.

18. An apparatus according to claim 16, wherein said display unit displays the first and second photographing limited regions upon superposing the regions with the 3D image.

19. An apparatus according to claim 16, wherein said display unit displays inner parts of the first and second photographing limited regions in colors different from those of outer parts of the regions.

20. An apparatus according to claim 16, wherein said 3D image data generating section comprises a section for rotating the 3D image data in accordance with a user instruction, and a section for limiting the rotation of the 3D image data on the basis of the data of the first and second photographing limited regions.

21. An apparatus according to claim 16, wherein said 3D image data generating section comprises a section for rotating the 3D image data in accordance with a user instruction, and a section for outputting an alarm signal when it is determined that said photographing unit at a position and an angle which correspond to a viewpoint and line-of-sight direction of the rotated 3D image data has entered the first and second photographing limited regions.

22. An apparatus according to claim 21, wherein said display unit displays a warning message when the alarm signal is output.

23. An apparatus according to claim 21, wherein a warning sound is generated when the alarm signal is output.

24. A radiographic image diagnosis apparatus comprising:
- a photographing unit having a radiation source and a 2D radiation detector to generate data of a fluoroscopic image of an object to be examined;
- a support mechanism configured to movably support said photographing unit;
- a 3D image data generating section configured to generate 3D image data corresponding to a position and angle of said photographing unit with respect to the object;
- a photographing limited region data generating section configured to generate data of a photographing limited region of said photographing unit which is limited by a structural limitation of said support mechanism; and
- a displaying unit configured to display the data of the photographing limited region, together with the 3D image data.

25. A radiographic image diagnosis apparatus comprising:
- a photographing unit having a radiation source and a 2D radiation detector to generate data of a fluoroscopic image of an object to be examined;
- a 3D image data generating section configured to generate 3D image data corresponding to a position and angle of said photographing unit with respect to the object;
- a photographing limited region data generating section configured to generate data of a photographing limited region of said photographing unit which is limited by a physique of the object; and
- a displaying unit configured to display the data of the photograph limitation region, together with the 3D image data.

\* \* \* \* \*